United States Patent
Cheucle et al.

(10) Patent No.: US 11,747,328 B2
(45) Date of Patent: *Sep. 5, 2023

(54) METHOD FOR MEASURING THE PLASMA CONCENTRATION OF AN ANALYTE DIRECTLY ON A WHOLE BLOOD SAMPLE

(71) Applicant: BIOMERIEUX, Marcy l'Etoile (FR)

(72) Inventors: Sylvie Cheucle, La Tour de Salvagny (FR); Laure Marillet, Lyons (FR); Aurélie Thollet, Nantes (FR)

(73) Assignee: BIOMERIEUX, Marcy L'Etoile (FR)

( * ) Notice: Subject to any disclaimer, the term of this patent is extended or adjusted under 35 U.S.C. 154(b) by 1352 days.

This patent is subject to a terminal disclaimer.

(21) Appl. No.: 16/169,158

(22) Filed: Oct. 24, 2018

(65) Prior Publication Data

US 2019/0056387 A1 Feb. 21, 2019

Related U.S. Application Data

(63) Continuation of application No. 14/787,790, filed as application No. PCT/FR2014/051086 on May 12, 2014, now Pat. No. 10,132,800.

(30) Foreign Application Priority Data

May 13, 2013 (FR) ...................... 1354276

(51) Int. Cl.
*G01N 33/543* (2006.01)
*G01N 33/68* (2006.01)
*G16B 40/10* (2019.01)
*G16B 40/00* (2019.01)

(52) U.S. Cl.
CPC ....... *G01N 33/543* (2013.01); *G01N 33/6887* (2013.01); *G16B 40/10* (2019.02); *G01N 2333/47* (2013.01); *G01N 2333/4706* (2013.01); *G01N 2333/75* (2013.01); *G16B 40/00* (2019.02)

(58) Field of Classification Search
None
See application file for complete search history.

(56) References Cited

U.S. PATENT DOCUMENTS

| | | |
|---|---|---|
| 2004/0018629 A1 | 1/2004 | Kawate |
| 2009/0177406 A1 | 7/2009 | Wu |
| 2009/0184004 A1 | 7/2009 | Chatelier et al. |
| 2010/0219084 A1 | 9/2010 | Blythe et al. |
| 2013/0068633 A1 | 3/2013 | Chatelier et al. |
| 2013/0098763 A1 | 4/2013 | Chatelier et al. |
| 2013/0199943 A1 | 8/2013 | Craggs et al. |
| 2015/0101928 A1 | 4/2015 | Chatelier et al. |

FOREIGN PATENT DOCUMENTS

| | | |
|---|---|---|
| CN | 101598702 A | 12/2009 |
| CN | 103096793 A | 5/2013 |
| EP | 1037048 A2 | 9/2000 |
| JP | 2002-071685 A | 3/2002 |
| JP | 2004-125775 A | 4/2004 |
| JP | 2009-168815 A | 7/2009 |
| JP | 2009-243955 A | 10/2009 |
| WO | 2008/040982 A1 | 4/2008 |
| WO | 2012/035297 A1 | 3/2012 |

OTHER PUBLICATIONS

Chinese Office Action and Search Report dated Sep. 20, 2016 in Chinese application No. 2014800280104, counterpart of parent U.S. Appl. No. 14/787,790 (with English machine translation; 27 pages).
Lamers et al., "Red blood cell folate concentrations increase more after supplementation with [6S]-5-methyltetrahydrofolate than with folic acid in women of childbearing age 1-4", The American Journal of Clinical Nutrition, XP-002719609, vol. 84, No. 1, Jul. 2006, pp. 156-161; cited in the ISR of parent U.S. Appl. No. 14/787,790.
Straseski et al., "Investigating Interferences of a Whole-Blood Point-of-Care Creatinine Analyzer: Comparison to Plasma Enzymatic and Definitive Creatinine Methods in an Acute-Care Setting", Clinical Chemistry, vol. 57, No. 11, Sep. 15, 2011, pp. 1566-1573; cited in the ISR of parent U.S. Appl. No. 14/787,790.
Flanagan et al., "Comparability of whole-blood and plasma clozapine and norclozapine concentrations", Journal of Clinical Pharmacology, vol. 56, Jan. 1, 2003, pp. 135-138; cited in the ISR of parent U.S. Appl. No. 14/787,790.

*Primary Examiner* — Joseph Woitach
(74) *Attorney, Agent, or Firm* — SECKEL IP, PLLC

(57) ABSTRACT

A method of measuring an analyte amount in a whole blood sample, including (i) measuring the haematocrit level of the whole blood sample; (ii) measuring an analyte amount directly in the whole blood sample; and (iii) calculating a corrected analyte amount according to relation $D_P = P_a(D_{ST}, D_H)$, where $D_P$ is the corrected analyte amount, $D_{ST}$ is the measured analyte amount, $D_H$ is the measured haematocrit level, and $P_a$ is a non-constant polynomial of a degree greater than or equal to 1 having as indeterminate values the measured analyte amount, $D_{ST}$, and the measured haematocrit level, $D_H$, and having its polynomial coefficients depending on the analyte.

8 Claims, 7 Drawing Sheets

METHOD FOR MEASURING THE PLASMA CONCENTRATION OF AN ANALYTE DIRECTLY ON A WHOLE BLOOD SAMPLE

This application is a continuation of U.S. application Ser. No. 14/787,790 filed Oct. 29, 2015, which is a national stage of PCT/FR2014/051086 filed May 12, 2014, each of which claims priority of France patent application No. 1354276 filed May 13, 2013, each of which is hereby incorporated by reference herein in its entirety.

FIELD OF THE INVENTION

The present invention relates to the analysis of biological samples, and more particularly to the measurement of the concentration or of the amount of an analyte in a blood sample. The invention particularly finds an application in immunoassay measurements of ELISA, ELFA, or immunocapture type.

BACKGROUND OF THE INVENTION

Usually, the search for an analyte of interest and for the concentration thereof in a whole blood sample likely to contain said analyte of interest comprises, first, separating the plasma from the red cells, particularly by centrifugation, and then measuring the analyte concentration in the plasma.

The "whole blood" corresponds to a biological sample comprising blood with all its components and thus, in particular, the plasma and the red cells. It may for example be blood sampled from a man or an animal without any transformation, or the same blood to which adjuvants have been added, for example, anticoagulants.

Among concentration measurement methods, techniques are known which comprise modifying a measurable property, for example, an optical, electrical, chemical, pH, or enzyme property, according to the quantity of analytes in a blood sample, especially so-called direct, indirect, and competitive ELISA ("Enzyme-Linked ImmnoSorbent Assay"), ELFA ("Enzyme-Linked Fluorescence Assay"), and immunocapture techniques.

FIG. 1 schematically illustrates the main steps of a direct ELISA measurement, also called "sandwich" ELISA since it involves two partners for binding to the analyte, where, for example, the analyte is an antigen and the two binding partners are antibodies each comprising a site, or epitope, different from each other and each capable of binding to said antigen provided with a complementary site. The ELISA measurement comprises, in its simplest version:
  coating the surface of a solid support, such as a well, for example, with a layer of a first binding partner of the analyte which is desired to be detected or the concentration of which is desired to be measured, where the first binding partner exhibits a site complementary to the analyte (FIG. 1A);
  pouring the blood sample, such as plasma originating from the centrifugation of a whole blood sample, into the well (FIG. 1B) so that the analytes present in the plasma conjugate with the first binding partners fixed to the well wall (FIG. 1C);
  performing a first washing of the well to remove the elements of no interest for the ongoing analysis, for example, antibodies and antigens which are not searched for (FIG. 1D);
  pouring into the well second binding partners for the analyte, each provided (i) with a site, complementary to one of the free sites of the analytes immobilized by means of the first binding partners and different from the complementary site of the first binding partner, and (ii) with a component having an enzyme function capable of catalyzing a hydrolysis of a substrate which changes color according to the quantity of catalyzed hydrogen (FIG. 1E). Such second binding partners containing an enzyme function are called "conjugates";
  performing a second washing of the well to remove excess conjugates (FIG. 1F);
  adding substrate degradable by the enzyme function of the conjugates into the well and measuring the chrominance or optical density of the medium contained in the well by spectrometry (FIG. 1G).

Since chrominance directly depends on the quantity or amount of analytes immobilized by the first binding partners fixed to the wall of the solid support, the measurement of this optical property thus is an indirect measurement of the total quantity of analytes present in the plasma sample, and accordingly, knowing the volume of the sample, of the analyte concentration therein. The measured chrominance is then transformed, by means of a predetermined mathematical model, into an amount and/or concentration value. "Amount" thus means a quantity of analytes in a sample. "Concentration" means an amount divided by the volume of the sample whereon the measurement is performed.

"Competitive" ELISA involves a single binding partner for the analyte, which exhibits a site complementary to one of the sites of the analyte, as well as a compound which competes with the analyte to be assayed. Once of these two elements then has an enzyme function capable of catalyzing a hydrolysis of a substrate which changes color according to the quantity of catalyzed hydrolysis. The amount and thus the concentration are thus inversely proportional to the read chrominance.

ELFA measurements are similar to ELISA measurements, but for the fact that the substrate catalyzed by the enzyme function generates fluorescence measured, for example, by a fluorometer.

All these measurement techniques provide elements only fixing the analytes having their concentration desired to be measured. Although only the latter are specifically fixed, it can however be observed that the nature of the sample substantially influences the amount measurement, especially when the reaction time is decreased due to diagnosis-related time constraints. Thus, when the measurement is directly performed on a whole blood sample, the measured amount is smaller than that which is directly measured on a plasma sample, particularly due to the presence of haematocrit, which has a matrix effect.

As known per se, the haematocrit level, or haematocrit, corresponds to the relative volume occupied by red cells relative to the whole blood volume. Certain manufacturers of immunoassay instrument using, as a sample for the diagnosis, a whole blood sample instead of a plasma sample, have provided correcting the analyte amount measured in a whole blood sample according to the following formula:

$$D_P = \frac{D_{ST}}{1 - \frac{D_H}{100}} \quad (1)$$

where $D_P$ is the corrected analyte amount, $D_{ST}$ is the analyte amount directly measured on a whole blood sample, $D_H$ is a measurement of the haematocrit level of the whole blood sample. It should be noted that relation (1) may also apply with the measured and corrected analyte concentrations instead of the corresponding amounts. However, such a correction, which is similar to a simple rule of three, does not provide good results.

To date, the amount of an analyte, and accordingly the concentration thereof, is thus mainly determined on plasma, this measurement being the only one considered as reliable and reproducible. Further, such a measurement has the advantage of being independent from the haematocrit level, which is variable from one subject to the other.

Now, the obtaining of plasma requires a prior centrifugation step, and thus time and specific equipment. Not only may time be a crucial parameter in the case of medical diagnosis, especially when there a threats on the subject's life, but this further assumes a large quantity of centrifuges in a laboratory in charge of a large number of analyses.

SUMMARY OF THE INVENTION

The present invention aims at providing a method of measuring the amount, and thus the concentration, of an analyte directly on a whole blood sample with a sufficient level of accuracy, thus enabling, in particular, to avoid the prior centrifugation step, while providing a measurement independent from the haematocrit level.

For this purpose, the invention aims at a method of measuring an amount of analyte in a whole blood sample, which comprises:
measuring the haematocrit level of the whole blood sample;
measuring an analyte amount directly in the whole blood sample; and
calculating a corrected analyte amount according to relation:

$$D_P = P_a(D_{ST}, D_H)$$

where $D_p$ is the corrected analyte amount, $D_{ST}$ is the measured analyte amount, $D_H$ is the measured haematocrit level, and $P_a$ is a non-constant polynomial of a degree greater than or equal to 1 having as indeterminate values the measured analyte amount, $D_{ST}$, and the measured haematocrit level, $D_H$, and having its polynomial coefficients depending on the analyte.

Once the analyte amount has been measured, the latter is usually translated, for example directly by the measurement instrument, into a concentration of analyte present in the sample, since the sample volume is fixed and known. Since the concentration value is used, particularly to implement an in vitro diagnosis, by comparing the measured concentration with predefined reference concentration values, characteristic of the diagnosis, the invention also aims at a method of measuring an analyte concentration in a whole blood sample, which comprises:
measuring the haematocrit level of the whole blood sample;
measuring an analyte amount directly in the whole blood sample and transforming it into a concentration based on the volume of the tested sample; and
calculating a corrected analyte concentration according to relation:

$$C_P = P_a(C_{ST}, D_H)$$

where $C_p$ is the corrected analyte concentration, $C_{ST}$ is the analyte concentration calculated from the measured amount and from the sample volume, $D_H$ is the measured haematocrit level, and $P_a$ is a non-constant polynomial of degree greater than or equal to 1 having as indeterminate values the analyte concentration obtained from the measured amount, $C_{ST}$, and the measured haematocrit level, $D_H$, and having its polynomial coefficients depending on the analyte.

In other words, the inventors have observed that it is possible to substantially correct the error on the amount/concentration directly measured on a whole blood sample by means of a non-constant polynomial, particularly of order greater than or equal to 1, having as unknowns, indeterminate values, or variables, the haematocrit level and the amount/concentration measured in the whole blood sample. The correction according to the invention especially enables to obtain a relative measurement error with respect to a measurement conventionally directly performed on a plasma sample contained and often comprised within +/−10% over a wide range of amounts/concentrations. The corrected amount/concentration, having a value sufficiently close to that which would have been obtained by performing the measurement directly on a plasma sample, can thus be used, for example, to perform an in vitro diagnosis so that it is no longer needed to carry out a prior centrifugation step.

According to an embodiment, polynomial $P_a$ comprises product $D_{ST} \times D_H$ of the measured analyte amount $D_{ST}$ by the measured haematocrit level $D_H$, or $C_{ST} \times D_H$ of the measured analyte concentration $C_{ST}$ by the measured haematocrit level $D_H$.

More particularly, the corrected analyte amount is calculated according to relation:

$$D_P = a_0 + a_1 \times D_{ST} a_2 \times D_H a_{12} \times D_{ST} \times D_H$$

where $a_0$, $a_1$, $a_2$ and $a_{12}$ are predetermined coefficients depending on the analyte.

In other words, the polynomial involving the interaction between terms $D_{ST}$ and $D_H$, that is, first order terms $D_{ST} \times D_H$, is particularly well adapted to ELISA, ELFA and immunocapture type immunoassay techniques.

Of course, coefficients $a_0$, $a_1$, $a_2$ and $a_{12}$ are also dependent on the measurement system (analyte and haematocrit).

Similarly, the corrected analyte concentration is calculated according to relation:

$$C_P = a'_0 + a_1 \times C_{ST} + a'_2 \times D_H + a_{12} \times C_{ST} \times D_H$$

where $a'_0$, $a_1$, $a'_2$ and $a_{12}$ are predetermined coefficients depending on the analyte.

In other words, the polynomial involving the interaction between terms $C_{ST}$ and $D_H$, that is, first order terms $C_{ST} \times D_H$, is particularly well adapted to ELISA, ELFA and immunocapture type immunoassay techniques.

Of course, coefficients $a'_0$, $a_1$, $a'_2$ and $a_{12}$ are also dependent on the measurement system (analyte and haematocrit).

Particularly, where the analyte is a D-dimer in a concentration measurement range from 45 ng/ml to 1,000 ng/ml, the coefficients are provided by the following relations:
$a'_0$ is in the range from $-29.311 \times 0.9$ to $-29.311 \times 1.1$;
$a_1$ is in the range from $0.788 \times 0.9$ to $0.788 \times 1.1$;
$a'_2$ is in the range from $0.702 \times 0.9$ to $0.702 \times 1.1$; and
$a_{12}$ is in the range from $0.018 \times 0.9$ to $0.018 \times 1.1$.
More specifically:
$a'_0 = -29.311$;
$a_1 = 0.788$;
$a'_2 = 0.702$; and
$a_{12} = 0.018$.

Particularly, where the analyte is a troponin, for example, cardiac troponin I, in a concentration measurement range from 0.01 µg/l to 1.6 µg/l, the coefficients are provided by the following relations:
$a'_0$ is in the range from $-0.0052 \times 0.9$ to $-0.0052 \times 1.1$;
$a_1$ is in the range from $0.9155 \times 0.9$ to $0.9155 \times 1.1$;

a'$_2$ is in the range from 0.0002×0.9 to 0.0002×1.1; and
a$_{12}$ is in the range from 0.0072×0.9 to 0.0072×1.1.
More specifically:
a'$_0$=−0.0052;
a$_1$=0.9155;
a'$_2$=0.0002; and
a$_{12}$=0.0072.

According to an embodiment, the measurement of the amount, and thus of the concentration of the analyte, is performed by an ELISA type or ELFA type or immunocapture type technique. In other words, the measurement technique used is not modified with respect to measurement techniques directly carried out on plasma. Immunoassay instruments of the state of the art can thus be used.

The invention also aims at a device for measuring the plasmatic amount of an analyte in a whole blood sample, characterized in that it comprises
  means for receiving said whole blood sample;
  means for measuring the total analyte amount in the whole blood sample;
  means for calculating a corrected analyte amount according to relation:

$$D_P = P_a(D_{ST}, D_H)$$

where $D_p$ is the corrected analyte amount, $D_{ST}$ is the measured analyte amount, $D_H$ is the measured haematocrit level, and $P_a$ is a non-constant polynomial of a degree greater than or equal to 1 having as indeterminate values the measured analyte amount, $D_{ST}$, and the measured haematocrit level, $D_H$, and having its polynomial coefficients depending on the analyte.

The invention also aims at a device for measuring the plasmatic concentration of an analyte in a whole blood sample, which comprises:
  means for receiving said whole blood sample;
  means for measuring the total analyte amount in the whole blood sample;
  means for transforming the analyte amount into a concentration;
  means for inputting or for measuring the haematocrit level in the whole blood sample; and
  means for calculating a corrected analyte concentration according to relation:

$$C_P = P_a(C_{ST}, D_H)$$

where $C_p$ is the corrected analyte concentration, $C_{ST}$ is the analyte concentration obtained from the measured amount, $D_H$ is the measured haematocrit level, and is a non-constant polynomial of a degree greater than or equal to 1 having as indeterminate values the measured analyte concentration $C_{ST}$ and the measured haematocrit level, and having its polynomial coefficients depending on the analyte.

BRIEF DESCRIPTION OF THE DRAWINGS

The invention will be better understood on reading of the following description provided as an example only in relation with the accompanying drawings, where.

DETAILED DESCRIPTION

Figure 1A:
FIGS. 1A to 1G are simplified views illustrating a state-of-the-art "sandwich" analyte concentration measurement of ELISA or ELFA type.
Figure 1B:
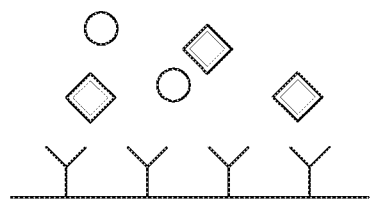
Figure 1C:
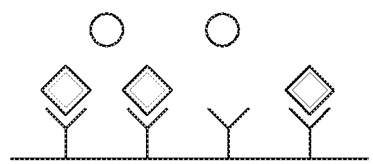
Figure 1D:
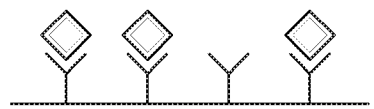
Figure 1E:
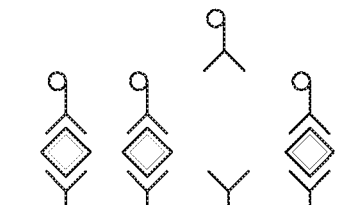
Figure 1F:
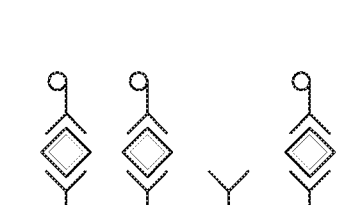
Figure 1G:
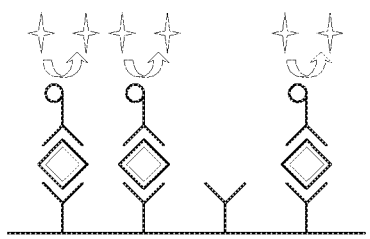
Figure 2:
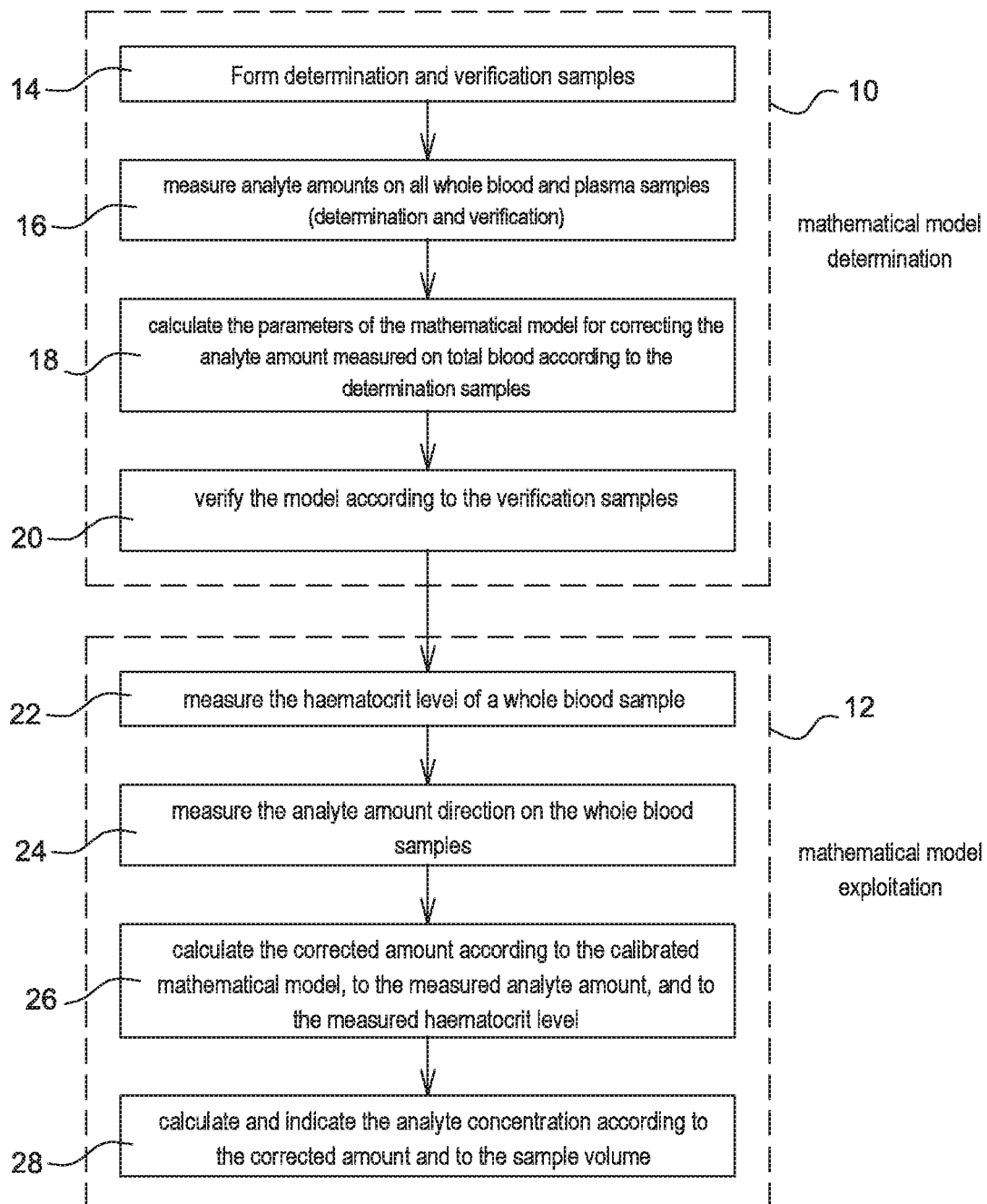
FIG. 2 is a flowchart illustrating a method according to the invention.

Referring to the flowchart of FIG. 2, a method according to the invention applied to a specific analyte will now be described.

The method comprises a step 10 of determining a mathematical model correcting the measurement of the analyte amount/concentration on a whole blood sample, and a step 12 of using the mathematical model determined at step 10 to deduce an unknown corrected analyte amount/concentration in a total blood sample sampled from a patient or an animal.

The determination of model 10 starts, at 14, with the forming of a set of pairs of whole blood and plasma samples originating from the same batch, for example, from the same patient or animal, with a variable haematocrit level and a variable analyte rate. The samples will be used to determine and verify the mathematical model. Advantageously, the haematocrit variation used for these samples is greater than the range observed for the person or the animal having given the blood, and preferably centered on the observed haematocrit average for the subject or a value close thereto. For example, the normal haematocrit values for man are from 40 to 54%, with an average at 45%, and from 37 to 47%, with an average at 42%, for woman, and the haematocrit level range used to determine and verify the mathematical model is in the range from 26% to 68%. The analyte concentration in the whole blood is selected to vary between a low value characteristic of a healthy subject and a high value prepared by overloading with a maximum 10% by volume of the whole blood sample.

For example, a set of whole blood volumes is formed and each volume is divided by two, the first sub-volume forming the whole blood sample and the second sub-volume being centrifuged to obtain the plasma sample. A whole blood volume may originate from a single subject, from a mixture of a plurality of whole bloods sampled from different subjects, it may be overloaded with analyte to set the analyte concentration, and/or originate from a first volume from which part of the plasma has been removed by centrifugation or to which plasma resulting from a centrifugation has been added to set the haematocrit level.

The method then carries on, at 16, for each pair of samples, by the measurement of the analyte amount or concentration and of the haematocrit level in the whole blood sample, and by measurement of the analyte amount or concentration in the corresponding plasma sample. The amounts are for example measured by means of technique of ELISA, ELFA, or immunocapture type of the state of the art. A set of triplets ($D_{ST}(i)$, $D_P(i)$, $D_H(i)$) is thus obtained, each comprising an amount $D_{ST}(i)$ of analyte in the whole blood, an amount $D_P(i)$ of analyte in the plasma, and a haematocrit level $D_H(i)$ in the whole blood. Of course, this can readily be applied to concentration measurement by replacing analyte amounts with analyte concentrations.

Advantageously, triplets having aberrant values are then discarded, particularly those for which amount $D_{ST}(i)$ measured in the whole blood is greater than amount $D_P(i)$ measured in the plasma. Here again, this is applicable to concentration measurement.

The obtained set of sample pairs is then divided into two subsets, containing an equal or different number, a first subset being used to determine the mathematical model and a second subset being used to verify the determined mathematical model. The samples used to determine the mathematical model are noted ($D_{ST}^{cal}(i)$, $D_p^{cal}(i)$, $D_H^{cal}(i)$) and the samples used to verify the mathematical model are noted ($D_{ST}^{verif}(i)$, $D_p^{verif}(i)$, $D_H^{verif}(i)$). For example, two thirds of the pairs of samples are used to determine the mathematical model and one third of the pairs is used for the verification thereof.

As known per se, the measurement technique used depends on the involved analyte, particularly due to the specific binding partners used to fix the analyte, for example, by immobilization at the surface of a solid surface, particularly a cone.

The measurement of the amount and of the concentration is implemented by means of one or a plurality of immunoanalyzers, such as for example BioMérieux's VIDAS® automaton. As known per se, an immunoanalyzer comprises one or a plurality of test sections capable of each receiving one or a plurality of test strips. Each strip comprises a plurality of wells, one well receiving the sample to be analyzed and the other wells respectively containing the reagents used during the measurement, particularly diluent, a rinsing solution, a solution comprising the conjugate, and a solution containing the enzyme substrate. The automaton further comprises a mechanism for displacing the strip under a cone having its surface containing a layer of binding partners specific to the analyte. The cone is then positioned above each well and pipets in a specific order the different mediums present therein while implementing intake, discharge, and incubation mechanisms specific to the measurement technique used. The automaton finally comprises a device for measuring the property implied in this technique. For example, the VIDAS® automaton applies an ELFA-type technique which differs from the previously-described direct ELISA technique in that the substrate catalyzed by the enzyme function generates fluorescence, and it comprises a fluorometer enabling to measure the fluorescence of the solution contain in the last cuvette once the last washing step has been carried out.

The haematocrit level is measured by means of any appropriate known technique, for example, by means of the so-called microhaematocrit technique used in the present embodiment, the Coulter technique, by laser measurement, or by conductivity measurement.

At a next step 18 of the method, a calculation is implemented according to the determination triplets, for example ($D_{ST}^{cal}(i)$, $D_p^{cal}(i)$, $D_H^{cal}(i)$), to calculate the parameters of a mathematical model for correcting an analyte amount directly measured from a whole blood sample, more particularly a model according to relation:

$$D_P = a_0 + a_1 \times D_{ST} a_2 \times D_H a_{12} \times D_{ST} \times D_H \quad (2)$$

where $D_p$ is the corrected analyte amount, $D_{ST}$ is the analyte amount directly measured on a whole blood sample, $D_H$ is the haematocrit level of the whole blood sample, and $a_1$, $a_2$, and $a_1$ are the calculated coefficients of the mathematical model.

Advantageously, before applying the polynomial coefficients calculation algorithm, variables $D_{ST}$ and $D_H$ of the polynomial according to relation (2) are normalized between −1 and 1. Particularly, if the analyte amount in the whole blood has as a minimum value $D_{ST}^{min}$ and has as a maximum value $D_{ST}^{max}$, variable $D_{ST}$ is transformed into variable:

$$X_{ST} = \frac{D_{ST} - c}{d}$$

where $$c = \frac{D_{ST}^{max} + D_{ST}^{min}}{2} \text{ and } d = \frac{D_{ST}^{max} - D_{ST}^{min}}{2}.$$

Similarly, if the haematocrit level has as a minimum value $D_H^{min}$ and has as a maximum value $D_H^{max}$, variable $D_H$ is transformed into variable $$X_H = \frac{D_H - e}{f},$$

with $$e = \frac{D_H^{max} + D_H^{min}}{2} \text{ and } f = \frac{D_H^{max} - D_H^{min}}{2}.$$

The model according to relation (2) can then be rewritten according to relation:

$$D_P = a_0'' + a_1'' \times X_{ST} + a_2'' \times X_H + a_{12}'' \times X_{ST} \times X_H \quad (3)$$

where coefficients $a_0''$, $a_1''$, $a_2''$ and $a_{12}''$ are determined according to the least square method by minimizing a cost function $f(D_p^{cal}(i) - (a_0'' + a_1'' \times X_{ST}^{cal}(i) + a_2'' \times X_H^{cal}(i) + a_{12}'' \times X_{ST}^{cal}(i) \times X_H^{cal}(i))$. Coefficients $a_0$, $a_1$, $a_2$ and $a_{12}$ can be easily deduced from coefficients $a_0''$, $a_1''$, $a_2''$ and $a_{12}''$ The transformation of the variables is independent from the calculation algorithm and enables to express each variable in the same scale and thus to compare the different coefficients $a_1''$, $a_2''$ and $a_{12}''$.

Here again, the foregoing is applicable to concentration measurement by replacing the analyte amount with an analyte concentration. Thus, as a variation, the analyte amount measured in the whole blood sample is transformed into an analyte concentration by dividing the measured amount by the volume of the whole blood sample, after which a mathematical concentration correction model is calculated, particularly a model according to relation:

$$C_P = a'_0 + a_1 \times C_{ST} + a'_2 \times D_H a_{12} \times C_{ST} \times D_H \quad (2\text{bis})$$

where $C_p$ is the corrected analyte concentration, $C_{ST}$ is the analyte concentration calculated from the measured amount and from the sample volume, and where $a'_0$, $a_1$, $a'_2$ and $a_{12}$ are predetermined coefficients depending on the analyte, these coefficients being for example calculated by a least square method. It should be noted that, since the analyte concentration is deduced from the amount, the coefficients linked to the analyte concentration in the polynomial, that is, coefficients $a_1$ and $a_{12}$, are the same for the two models expressed in amount and in concentration. However, the other coefficients, that is, $a'_0$ and $a'_2$, are different.

Similarly, it is possible to apply a normalization of the variables of the polynomial of relation (2bis) similar to the normalization of relation (3), by calculating a mathematical model according to relation:

$$C_P = a_0''' + a_1''' \times Y_{ST} + a_2''' \times X_H + a_{12}''' \times Y_{ST} \times X_H \quad (3\text{bis})$$

where $$Y_{ST} = \frac{C_{ST} - g}{h}, \quad g = \frac{C_{ST}^{max} + C_{ST}^{min}}{2}, \quad h = \frac{C_{ST}^{max} - C_{ST}^{min}}{2},$$

$C_{ST}^{min}$ is the minimum value of concentration $C_{ST}$, $C_{ST}^{max}$ is the maximum value of concentration $C_{ST}$, and the polynomial coefficients are coefficients which can easily be deduced from the polynomial coefficients of relation (2bis).

The method then carries on, at 20, with the verification of the determined model by using the set of verification triplets, for example, $(D_{ST}^{verif}(i), D_p^{verif}(i), D_H^{verif}(i))$ for the amount model.

More particularly, the determined model is advantageously verified based on at least one of the following criteria:
relative error $$\frac{D_P^{cor}(i) - D_P^{verif}(i)}{D_P^{verif}(i)}$$

between amount $D_p^{cor}(i)$ corrected by the mathematical model, that is, $D_p^{cor}(i) = a_0 + a_1 \times D_{ST}^{verif}(i) + a_2 \times D_H^{verif}(i) + a_{12} \times D_{ST}^{verif}(i) \times D_H^{verif}(i)$, and amount $D_p^{verif}$ measured in the plasma. More particularly, it is verified whether the relative error is centered on 0% and is in the range from −10% to +10%;

the parameters of a linear equation, for example, obtained according to a so-called "Passing and Bablok" linear regression, $D_p^{cor}(i) = \alpha + \beta \times D_p^{verif}(i)$; and biases calculated for different analyte amounts in the plasma by using the above-described "Passing and Bablok" equation.

Here again, the foregoing can readily be applied to concentration measurement by replacing the analyte amount with an analyte concentration.

Once the determined model has been validated, the method carries on with the exploitation, at 12, of this model for the analyte amount/concentration measurement directly performed on whole blood samples.

For example, the model is embarked in the data processing unit of an immunoanalyzer available for sale which may further be modified to be able to receive or calculate haematocrit level values. Otherwise, the model is implemented on a processing unit independent from the immunoanalyzer, for example, a personal computer. In this variation, an operator inputs into the unit the analyte amount/concentration value measured by the immunoanalyzer on a whole blood sample and the value of the haematocrit level measured for this sample and obtains in return the corrected analyte amount/concentration.

Thus, for a whole blood sample of known volume for which the amount, and above all the concentration, of analyte is desired to be known, exploitation step 12 starts, at 22, with the measurement of haematocrit level $D_H$ of the sample and carries on, at 24, with the measurement of the analyte amount/concentration directly in the whole blood sample by means of the same measurement technique, implemented by a same immunoanalyzer model as that used to determine and verify the mathematical model.

A corrected analyte amount $D_p$ is then calculated, at 26, according to relation (2) with coefficients $a_0$, $a_1$, $a_2$, and $a_{12}$ calculated on determination of model 10, or equivalently coefficients $a_0''$, $a_1''$, $a_2''$ and $a_{12}''$ of the model according to relation (3) A corrected analyte concentration is calculated in the same way according to relation (2bis) or (3bis).

At 28, the concentration is calculated and then output, for example, displayed on a screen and/or recorded in a computer memory. Optionally, the corrected amount may also be output.

A method according to the invention where the measured amount or concentration is corrected by a mathematical model has been described.

As previously described, measurement techniques are based on the measurement of a property, for example, an optical, electrical, chemical, pH, or enzyme-linked property, having its value depending on the analyte amount present in the analyzed sample. An immunoanalyzer thus comprises a device which measures such a property and outputs a signal corresponding to this measurement. According to the state of the art, the signal is then processed by means of a predetermined mathematical model which transforms the signal into an amount and/or concentration value.

As a variation, the method applies to the actual signal, before the transformation thereof. Particularly, the signal measured on the whole blood sample is corrected according to relation:

$$S_P = a_0 + a_1 \times S_{ST} + a_2 \times D_H a_{12} \times S_{ST} \times D_H \quad (4)$$

where $S_p$ is the corrected signal and $S_{ST}$ is the signal originating from the measurement on the whole blood sample. The method applied to the signal correction is similar to the previously-described method, provided to make minor modifications within the abilities of those skilled in the art. The calculation of a mathematical model with normalized variables similar to relation (3) is also possible.

Two examples of application of the invention, respectively an application to the measurement of a D-dimer concentration and an application to the measurement of a cardiac troponin I concentration will now be described.

Measurement of the D-Dimer Concentration

D-dimers are heterogeneous fibrin products all having epitope D-D formed by two continuous fibrin monomers covalently bonded by the enzyme responsible for the blood coagulation crosslinking fibrin, or "XIIIa" factor. The assaying of D-dimers is mainly indicated in the diagnosis of exclusion of venous thromboembolic diseases, particularly deep venous thrombosis and pulmonary embolism, the evaluation of the risk of recurrence of such diseases after the stopping of an anticoagulant treatment, and in the diagnosis of disseminated intravascular coagulation.

To determine and verify the mathematical model associated with the D-dimer, blood has been sampled from 186 healthy subjects on sodium citrate as an anticoagulant. More particularly, the blood has been collected in tubes of 4.5 mL under vacuum containing 0.129 M of trisodium citrate.

In order to have whole blood samples with a varied haematocrit level, the collected samples have been diluted with their own plasma after a light centrifugation, to obtain a haematocrit level varying in the range from 26% to 61%. The haematocrit level is measured by means of the microhaematocrit technique. The microhaematocrit is first acquired by centrifugation of capillaries for 7 minutes at 10,000 rpm, after which the value of the haematocrit level is then deduced by means of a chart, as know per se in the state of the art.

Figure 3:
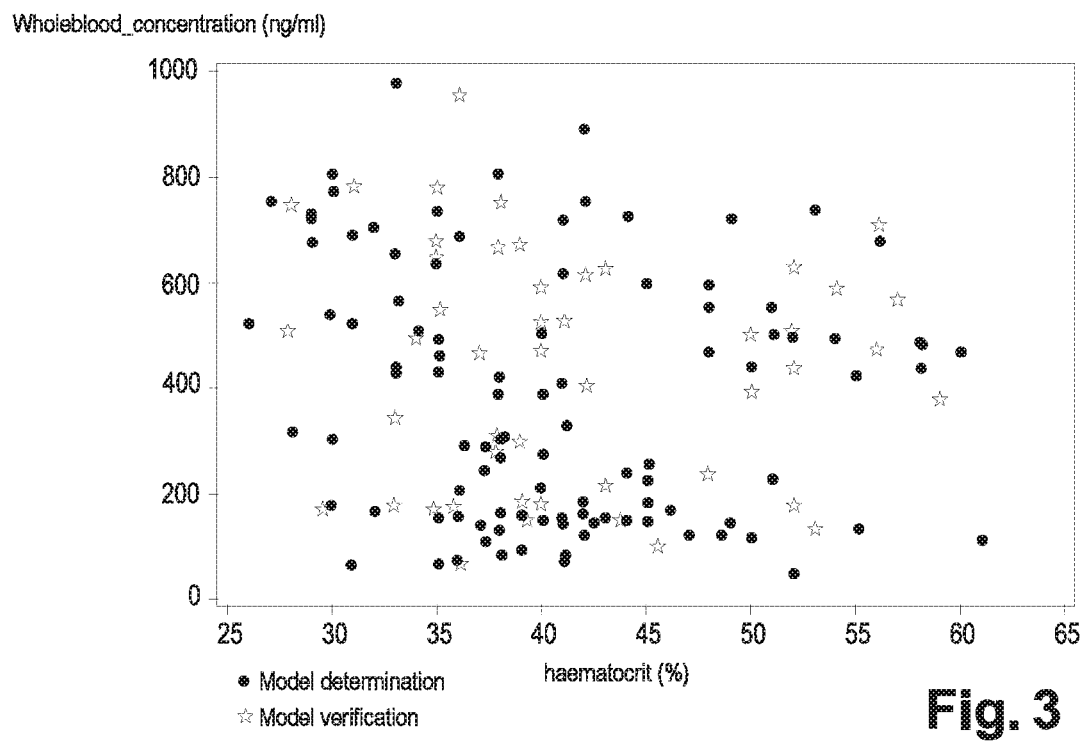
FIG. 3 is a plot illustrating the concentration and haematocrit level homogeneity of samples used to determine and verify a polynomial correction model applied to D-dimers.

In order to have whole blood and plasma samples with a varied D-dimer concentration, the whole blood samples have been overloaded with D-dimer, before or after having varied the haematocrit level. To overload the samples, plasmas from bioMérieux's internal serum bank (Marcy L'Etoile, France) with a strong D-dimer concentration to be assayed have been used to have a distribution of the D-dimer concentration in the whole blood in the 45 ng/mL-1,000 ng/mL range. The whole blood samples have been overloaded, particularly to 300 ng/mL, 500 ng/mL, and 1,000 ng/mL, with an overload which does not exceed 10% of the volume of the whole blood sample to avoid modifying the original blood matrix, that is, which does not exceed 1,000 ng/mL. The sample distribution is uniform in the D-dimer concentration range obtained from the amount measured in the whole blood and in the haematocrit level range, as illustrated in FIG. 3, which shows the (concentrations originating from the amounts measured in the whole blood, haematocrit level) pairs for the model determination triplets (dots) and for the model verification triplets (stars) The plasma samples are further obtained by centrifugation of a portion of each whole blood sample at 3,000 rpm for 10 minutes.

As a numerical example, after the preparation of samples, the D-dimer concentration in the whole blood is distributed in the range from 46.78 ng/mL to 982.81 ng/mL, the haematocrit level is distributed in the range from 26% to 61%, and the D-dimer concentration in the plasma is distributed in the range from 96.86 ng/mL to 1,419.58 ng/mL.

The measurement of the D-dimer concentration in the whole blood and plasma samples comprises the enzyme immunoassay of fibrin degradation products (PDF) in human plasma by an ELFA-type technique, particularly implemented by a VIDAS® automaton with the "VIDAS D-dimère Exclusion II" kit designated with reference 30 455 of bioMérieux SA. Such a measurement thus associates the sandwich-type enzyme immunoassay method in two steps with a final fluorescent detection (ELFA). In a first step, the sample is sampled, aspirated, and discharged a plurality of times so that the antigen can bind to the anti-FbDP antibodies (FbDP for "fibrinogen degradation products") fixed on the cone. In a second step, a monoclonal anti-FbDP antibody marked with ALP (alkaline phosphatase) binds to the antigen already fixed on the cone to form a sandwich. Washing steps eliminate the non-fixed or excess compounds The development step is then carried out. The 4MUP substrate (4-methyl-umbelliferyl-phosphate) is sucked in and then discharged into the cone and the ALP catalyses the hydrolysis of the substrate into fluorescent 4MU (4-methyl-umbelliferone). The emitted fluorescence is measured at 450 nm. The value of the fluorescence signal is proportional to the antigen amount in the sample.

Figure 4:
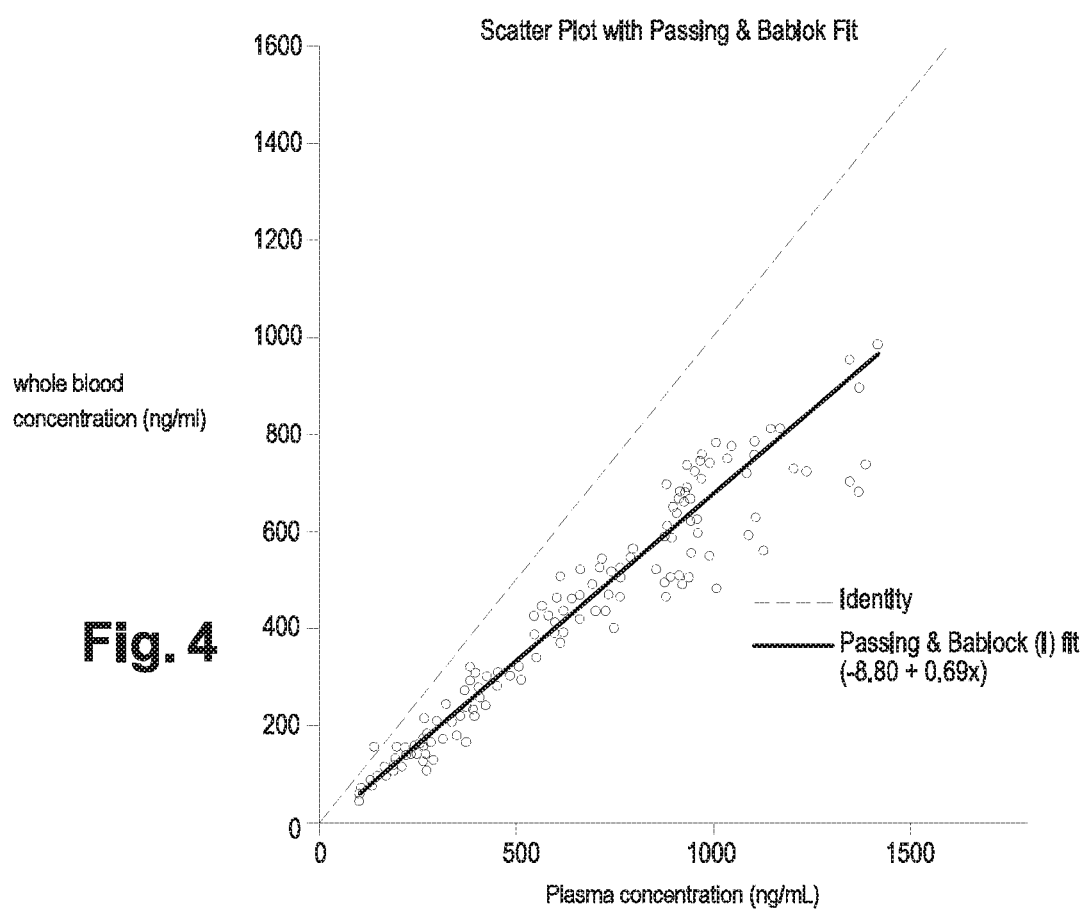
FIG. 4 is a plot illustrating the D-dimer concentration measured in whole blood, with no correction according to the invention, according to the measured D-dimer concentration of the plasma.

FIG. 4 illustrates the D-dimer concentrations obtained from concentrations $C_{ST}(i)$ measured in the whole blood samples according to the D-dimer concentrations obtained from amounts $C_p(i)$ measured in the respective plasma samples. A "Passing and Bablok"-type linear regression $C_{ST}(i)=\alpha+\beta \times C_p(i)$ between the two amounts particularly provides $\alpha=-8.80$ and $\beta=0.69$.

The triplets for which the concentrations measured in the whole blood are greater than the concentrations in the plasma have been discarded.

One hundred and three triplets $(C_{ST}^{cal}(i), C_p^{cal}(i), C_H^{cal}(i))$ have been used to determine the mathematical model.

The following coefficients are thus obtained:

$a_0'=806.279$;
$a_1''=803.998$ with a standard deviation equal to 11.917;
$a_2'=196.295$ with a standard deviation equal to 12.389; and
$a_{12}''=182.254$ with a standard deviation equal to 25.909, or, equivalently, with no normalization:

$a_0'=29.311$;
$a_1=0.788$;
$a_2'=0.702$; and
$a_{12}=0.018$.

Fifty verification triplets $(C_{ST}^{verif}(i), C_p^{verif}(i), C_H^{verif}(i))$ have further been used to verify the mathematical model.

Figure 5:
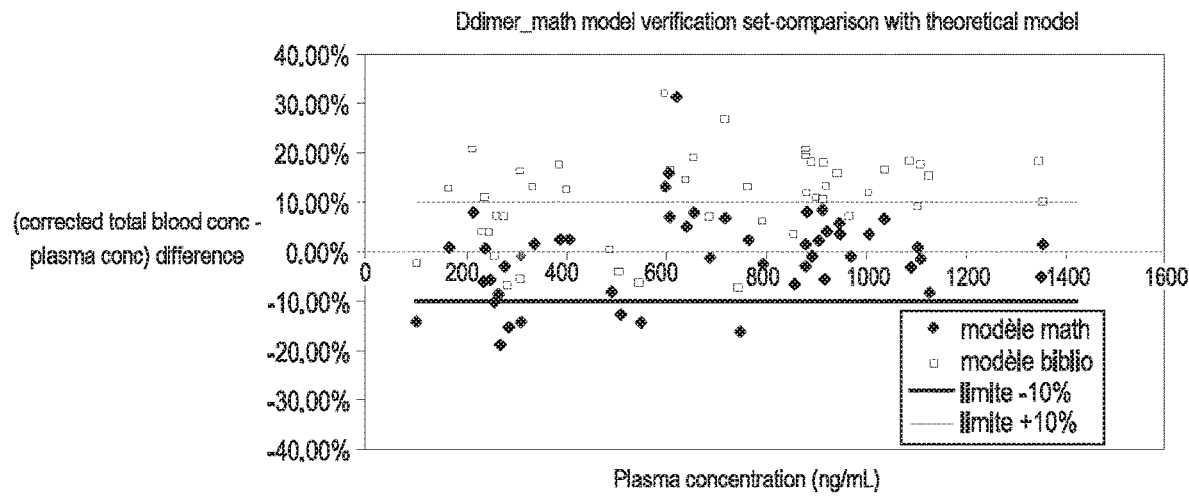
FIG. 5 is a plot, for the samples of the verification set, of the relative correction error obtained according to the invention and according to a correction of the state of the art, according to the D-dimer concentration measured in plasma.

FIG. 5 illustrates relative error $$\frac{C_p^{cor}(i) - C_p^{verif}(i)}{C_p^{verif}(i)}$$

according to the D-dimer concentration obtained from the amount measured in the plasma both for a correction $C_p^{cor}(i)$ according to relation (2bis) or (3bis) applied to the verification samples, represented by diamonds, and for a correction $C_p^{cor}(i)$ of the state of the art performed according to relation (1) applied to the verification samples, represented by squares. As can be noted, conversely to the correction of the state of the art, the relative error obtained by the invention is centered on zero, and is mainly in the range from −10% to 10%.

Figure 6:
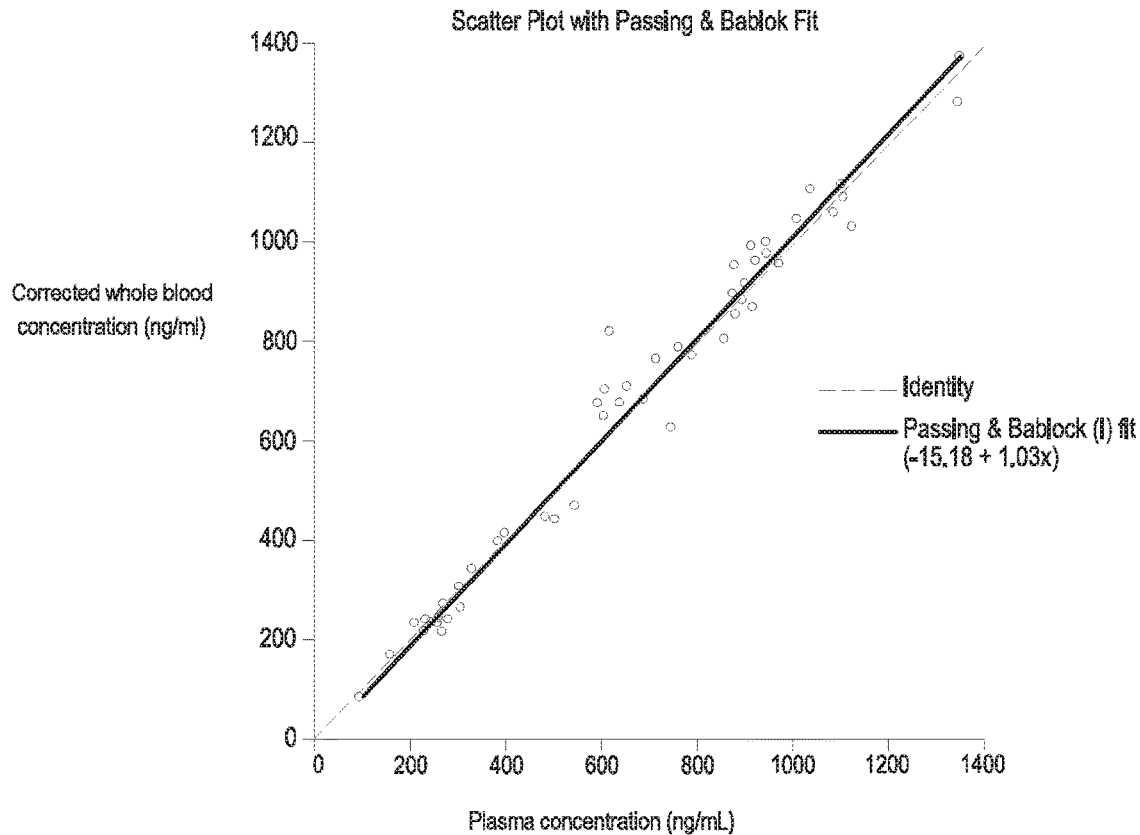
FIG. 6 is a plot, for the samples of the verification set, of the D-dimer concentration corrected according to the invention according to the D-dimer concentration measured in plasma.
Figure 7:
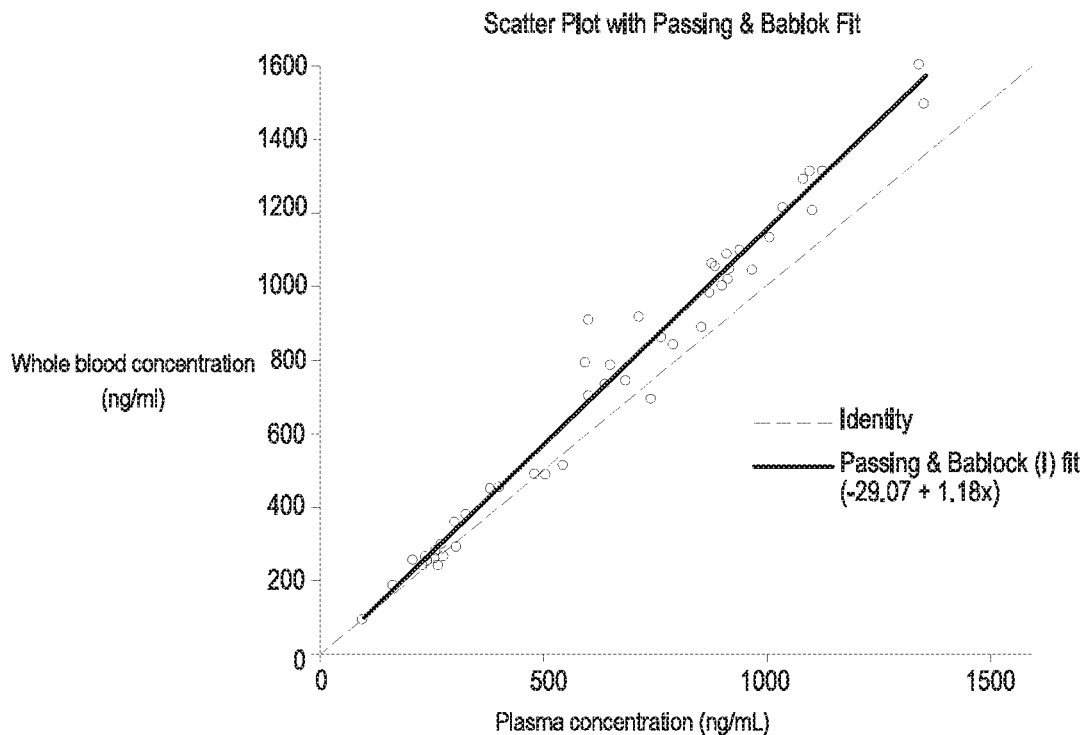
FIG. 7 is a plot of the D-dimer concentration corrected according to the state of the art according to the D-dimer concentration measured in plasma.

FIGS. 6 and 7 illustrate the corrected concentrations according to the concentrations measured on plasma respectively according to the correction of relation (2bis) or (3bis) and according to the correction of relation (1), and applied to the verification samples. The line obtained by linear regression of "Passing and Bablok" type for each of the corrections is further calculated and plotted. The line corresponding to the correction of the state of the art has a slope equal to 1.18. The line corresponding to the invention is close to identity with a slope equal to 1.03.

Finally, the biases for three D-dimer concentrations in the whole blood, that is, 250 ng/mL, 500 ng/mL, and 1,000 ng/mL, have been calculated and are respectively equal to −3.4%, −0.4%, and +1.1% for the correction according to the invention, and are respectively equal to +6.7%, +12.5%, and +15.4% for the correction of the state of the art.

Concentrations corrected according to the invention similar to those obtained by a measurement directly performed on plasma can thus be observed.

Similar results can be observed when the correction is performed on the signal measured on the samples.

Measurement of the Cardiac Troponin I Concentration

Troponins (Tn) are proteins of the striated muscle. The striated muscle is formed of a thick filament, made of myosin, and of a thin filament made of actin, of tropomyosin, and or the troponin complex. This complex is itself formed of three sub-units, that is, the so-called "C", "I", and "T" troponins. Each of these troponins has skeletal and cardiac isoforms. Cardiac troponins are choice markers for the detection of myocardial necrosis and the assaying thereof enables to diagnose a myocardial infarction. The assaying of cardiac troponins is also used for the follow-up of a thrombolytic treatment and to estimate the size of the myocardial necrosis, as well as in the diagnosis of acute coronary syndromes. The assaying of troponin "I", noted TnI, also enables to highlight a heart impairment in the context of other pathologies, particularly a renal failure, hypothyroidism, collagenoses, myopathies, or also pulmonary embolism.

To determine and verify the mathematical model associated with TnI, blood has been sampled from 186 healthy subjects on lithium heparinate as an anticoagulant. More particularly, the blood has been collected in tubes of 4 mL containing 17 UI/mL of lithium heparinate.

The obtaining of whole blood samples with haematocrit levels and TnI concentrations, and the obtaining of plasma samples from the whole blood samples are similar to those described in relation with the dosage of D-dimers.

The measurement of the TnI concentration in the whole blood and plasma samples comprises the enzyme immunoassay of troponin in human plasma by an ELFA-type technique, particularly implemented by a VIDAS® automaton with the "VIDAS Troponine I Ultra" kit designated with reference 30 448 of bioMérieux. In a single step, the sample is sampled and transferred into the well containing the conjugates which are anti-TNI cardiac antibodies marked with ALP. The sample/conjugate mixture is sucked in and then discharged a plurality of times by the cone. This enables the TnI, on the one hand, to bind to the conjugate to form a sandwich. Washing steps eliminate the non-fixed or excess compounds. The ALP catalyzes the hydrolysis of the substrate contained in the last well of the VIDAS® strip into fluorescent 4MU. The emitted fluorescence is measured at 450 nm. The value of the fluorescence signal is proportional to the antigen concentration in the sample. At the end of the test, the results are calculated from two calibration curves corresponding to the two development steps. A threshold signal manages the selection of the calibration curve to be used for each sample.

The TnI concentration in the whole blood samples varies from 0.01 µg/L to 1.4 µg/L and the haematocrit level varies from 22% to 73%, the TnI concentration in the plasma thus varying from 0.01 µg/l to 1.6 µg/l.

Figure 8:
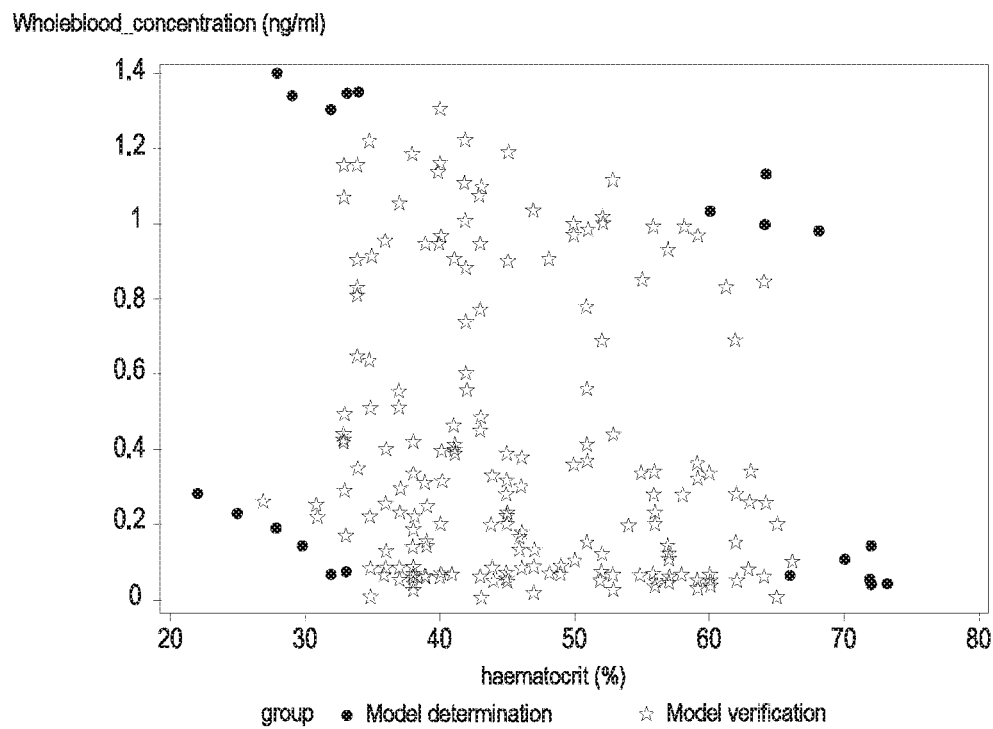
FIG. 8 is plot, for the samples of the determination and verification sets, illustrating the concentration and haematocrit level homogeneity of samples used to determine a polynomial correction model applied in the context of the quantification of cardiac troponin I (TnI)

The sample distribution is uniform in the TnI concentration range measured in the whole blood and in the haematocrit level range, as illustrated in FIG. 8, which shows the (concentrations measured in the whole blood, haematocrit level) pairs for the model determination triplets (dots) and for the model verification triplets (stars)

Figure 9:
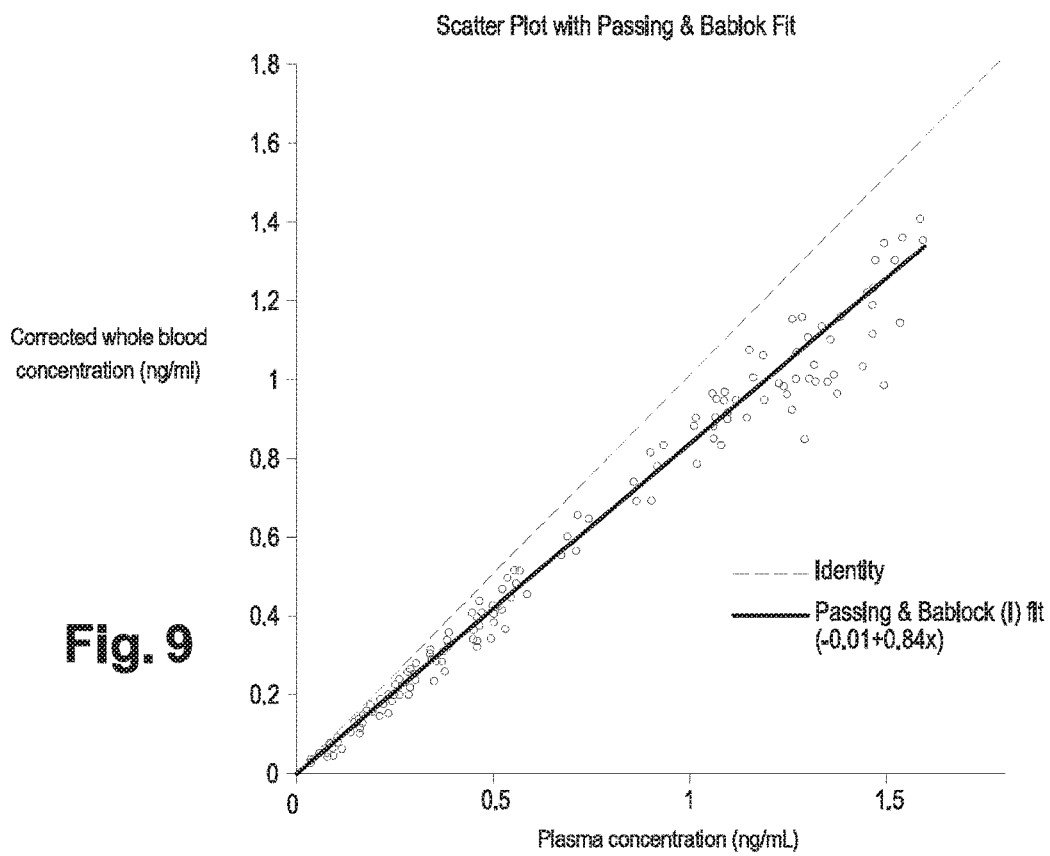
FIG. 9 is a plot illustrating the TnI concentration measured in whole blood samples, with no correction according to the invention, according to the TnI concentration measured in plasma samples.

FIG. 9 illustrates the TnI concentration $C_{ST}(i)$ obtained from concentrations measured in the whole blood samples according to the TnI concentration $C_p(i)$ measured in the respective plasma samples. A "Passing and Bablok"-type linear regression $\alpha=-0.01$ between the two concentrations particularly provides $\alpha=-0.01$ and $\beta=0.84$.

A total one hundred and eighty-seven samples have been prepared and an exchange algorithm, for example, a Fedorov algorithm, is implemented, for example, by software NEM-RODW® of LPRAI Sarl. The Fedorov algorithm is an iterative algorithm which has the advantage of enabling to select the N best samples to determine the mathematical model, for example, the 20 best samples among all the samples to calculate the parameters of the mathematical model.

The following coefficients are obtained by means of the twenty selected samples:

$a_0'=0.8982$;
$a_1''=0.86751$;
$a_2'=0.1334$; and
$a_{12}''=0.12413$.
or equivalently:
$a_0'=-0.0052$;
$a_1=0.9155$;
$a_2'=0.0002$; and
$a_{12}=0.0072$.

One hundred and sixty-seven verification triplets ($C_{ST}^{verif}(i)$, $C_p^{verif}(i)$, $C_H^{verif}(i)$) have further been used to verify the mathematical model.

Figure 10:
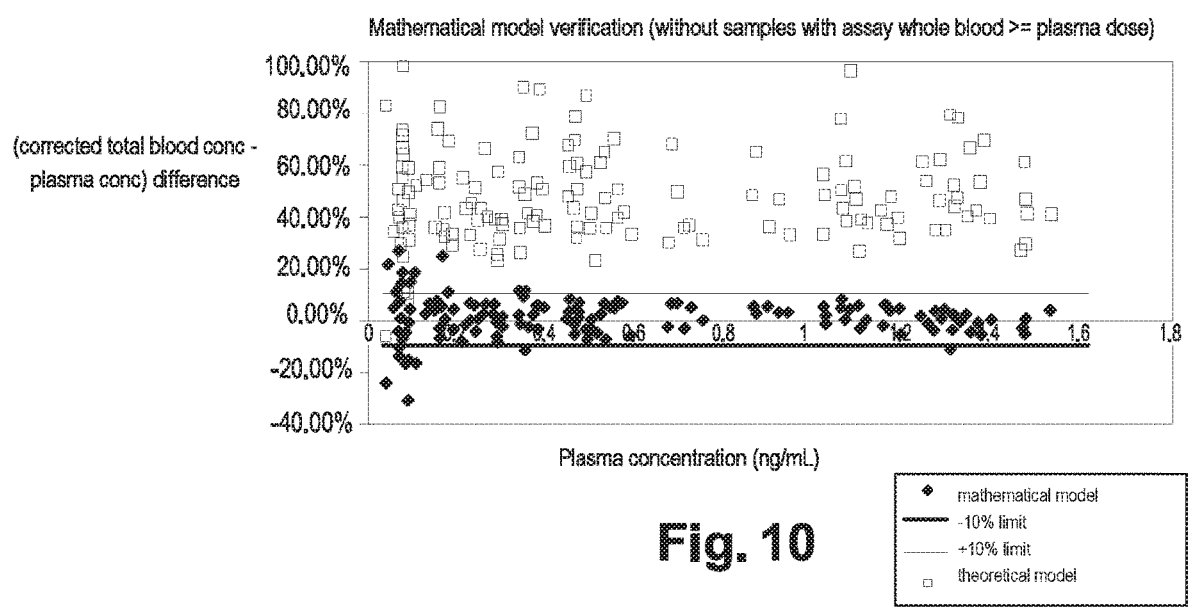
FIG. 10 is a plot, for the samples of the verification set, of the relative correction error obtained according to the invention and according to a correction of the state of the art, according to the TnI concentration measured in plasma.

FIG. 10 illustrates relative error $$\frac{C_p^{cor}(i) - C_p^{verif}(i)}{C_p^{verif}(i)}$$

according to the TnI concentration obtained from the amount measured in the plasma both for a correction $C_p^{cor}(i)$ according to relation (2bis) or (3bis) applied to the verification samples, represented by diamonds, and for a correction $C_p^{cor}(i)$ of the state of the art performed according to relation (1) applied to the verification samples, represented by squares. As can be noted, conversely to the correction of the state of the art, the relative error is centered on zero, and is mainly in the range from −10% to 10%. A few results outside of −/+10% in the sample range where the TnI concentration is close to the detection limit can be observed.

Figure 11:
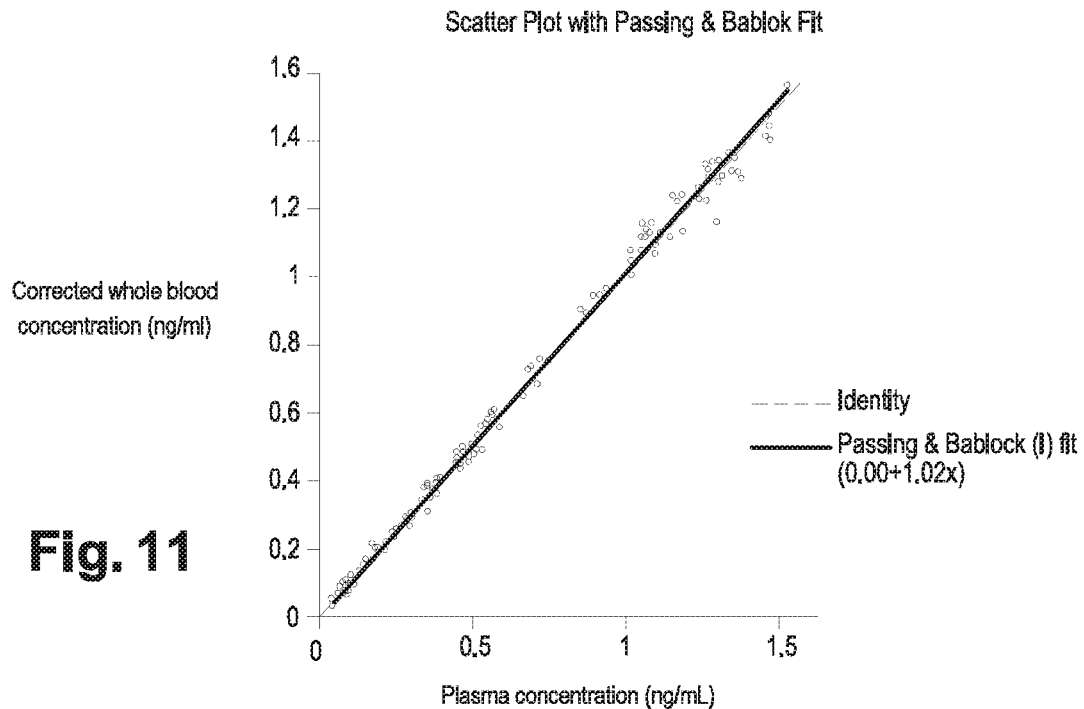
FIG. 11 is a plot of the TnI concentration corrected according to the invention according to the TnI concentration measured in plasma.
Figure 12:
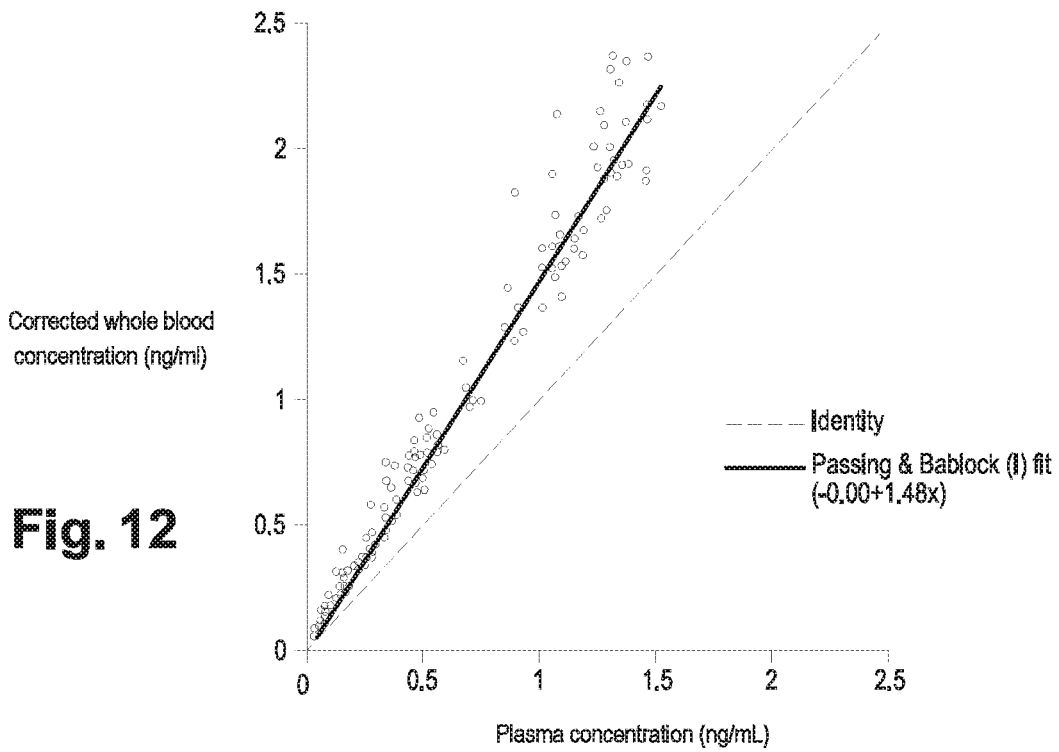
FIG. 12 is a plot of the corrected TnI concentration according to the state of the art according to the TnI concentration measured in plasma.

FIGS. 11 and 12 illustrate the corrected TnI concentrations according to the concentrations measured on plasma respectively according to the correction of relation (2bis) or (3bis) and the correction of relation (1), and applied to the verification samples. The line obtained by linear regression of "Passing and Bablok" type for each of the corrections is further calculated and plotted. The line corresponding to the correction of the state of the art has a slope equal to 1.48. The line corresponding to the invention is close to identity with a slope equal to 1.02.

Finally, the biases for three TnI concentrations in the whole blood, that is, 0.1 µg/L, 0.5 µg/L, and 1 µg/L, have been calculated and are respectively equal to 3.1%, 2.0%, and +1.9% for the correction according to the invention, and are respectively equal to +43.3%, +46.7%, and +47.1% for the correction of the state of the art.

The same results as those obtained for D-dimers can also be observed, that is, corrected concentrations which are similar to those obtained by a measurement directly performed on plasma.

Similar results can be observed when the correction is performed on the signal measured on the samples.

Embodiments where a polynomial of first degree according to relation (2bis) or relation (3bis) is used have been described. A second degree polynomial comprising the square of the haematocrit level and/or the square of the analyte amount/concentration measured in the whole blood may also be used. Similarly, a polynomial of higher degree may be used.

Particularly, the following procedure may be used to identify the polynomial used:
 a) setting the order of the polynomial to 1;
 b) calculating the parameters of the polynomial, for example, by means of a least square method, as previously described;
 c) if the prediction error of the polynomial is considered satisfactory, selecting this polynomial. For example, the prediction error is calculated and if it is lower than a threshold, advantageously 10%, the polynomial is selected; and
 d) if the prediction error, advantageously calculated on a set of verification data, is not considered satisfactory, increasing the order of the polynomial by one unit and repeating steps b), c), and d) until the prediction error is considered satisfactory. As a variation, these steps are repeated as long as the order is smaller than or equal to 10, and preferably smaller than or equal to 5.

Of course, other methods of calculation and/or of final selection of the polynomial may be used. For example, the order may also be calculated by means of a non-linear regression, as known per se in the state of the art. Similarly, a bayesian-type criterion, for example, the BIC ("bayesian information criterion"), may be used to select the final polynomial when a plurality of polynomials have been calculated.

Embodiments where the amount/concentration measurement is used with no transformation of the variables in the mathematical models have been described. As a variation, a transformation of the measurement space may be implemented, for example, a logarithmic transformation if the measured amount/concentration range is significant. Term "measurement" thus means, in the sense of the invention, the direct or transformed measurement.

Similarly, polynomial coefficients calculated for a significant amount/concentration range have been described. As a variation, the range of amounts/concentrations may be divided into a plurality of intervals and a mathematical model may be determined for each of these intervals. The coefficients of the model may thus depend on the amount/concentration interval for which they are calculated.

The invention claimed is:

1. A method of performing a calibration of the device for measuring an amount of analyte in a whole blood sample, wherein the method comprises:
 providing a plurality of calibration whole blood samples and performing measurements on the calibration whole blood samples, wherein the measurements include, for each of the plurality of calibration whole blood samples:
  measuring an haematocrit level in the calibration whole blood sample;
  measuring an analyte amount in the calibration whole blood sample; and
  measuring an analyte amount in a plasma sample obtained from the calibration whole blood sample; and
 calculating polynomial coefficients of a calibrated relation:

$$D_P = P_a(D_{ST}, D_H)$$

from values of haematocrit level and analyte amount measured in the plurality of calibration whole blood samples, and values of analyte amount measured in the plasma samples obtained from the plurality of calibration whole blood samples,
 where $D_p$ is the measured analyte amount in plasma, $D_{ST}$ is the measured analyte amount in whole blood, $D_H$ is the measured haematocrit level, and $P_a$ is a non-constant polynomial of a degree greater than or equal to 1 having as indeterminate values the measured analyte amount, $D_{ST}$, and the measured haematocrit level, $D_H$, the polynomial coefficients depending on the analyte,
 wherein, after calibration, the device, upon receiving a measurement of a total analyte amount in a whole blood sample, calculates a corrected analyte amount according to the calibrated relation $D_P = P_a(D_{ST}, D_H)$,
 where $D_p$ is the corrected analyte amount, $D_{ST}$ is the measured analyte amount, and $D_H$ is the measured haematocrit level.

2. The method of claim 1, wherein polynomial $P_a$ comprises product $D_{ST} \times D_H$ of the measured analyte amount $D_{ST}$ by the measured haematocrit level $D_H$.

3. The method of claim 1, wherein the analyte amount is measured according to an immunoassay technique of ELISA type, of ELFA type, or of immunocapture type.

4. A method of performing a calibration of the device for measuring an analyte concentration in a whole blood sample, wherein the method comprises:
 providing a plurality of calibration whole blood samples and performing measurements on the calibration whole blood samples, wherein the measurements include, for each of the plurality of calibration whole blood samples:
  measuring an haematocrit level in the calibration whole blood sample;
  measuring an analyte amount in the calibration whole blood sample, and obtaining an analyte concentration in the calibration whole blood sample by dividing the analyte amount measured in the calibration whole blood sample by a volume of the calibration whole blood sample; and
  measuring an analyte amount in the plasma sample, and obtaining an analyte concentration in a plasma sample from the calibration whole blood sample by dividing the analyte amount measured in the plasma sample by a volume of the plasma sample;
 calculating a corrected analyte concentration according to a calibrated relation:

$$C_P = P_a(C_{ST}, D_H)$$

from values of haematocrit level and analyte concentration measured in the plurality of calibration whole blood samples, and values of analyte concentration measured in the plasma samples from the plurality of calibration whole blood samples,
 where $C_p$ is the analyte concentration calculated from the measured analyte amount in plasma, $C_{ST}$ is the analyte concentration calculated from the measured analyte amount in whole blood, $D_H$ is the measured haematocrit level, and $P_a$ is a non-constant polynomial of a degree greater than or equal to 1 having as indeterminate values the measured analyte concentration, $C_{ST}$, and the measured haematocrit level, $D_H$, the polynomial coefficients depending on the analyte, wherein, after calibration, the device, upon receiving a measurement of a total analyte concentration in a whole blood sample, calculates a corrected analyte concentration according to the calibrated relation $C_P=P_a(C_{ST}, D_H)$, where $C_p$ is the corrected analyte concentration, $C_{ST}$ is the measured analyte concentration, and $D_H$ is the measured haematocrit level.

5. The method of claim 4, wherein polynomial $P_a$ comprises product $C_{ST} \times D_H$ of the measured analyte concentration $C_{ST}$ by the measured haematocrit level $D_H$.

6. The method of claim 4, wherein the analyte concentration is measured according to an immunoassay technique of ELISA type, of ELFA type, or of immunocapture type.

7. A device for measuring the plasmatic amount of an analyte in a whole blood sample, wherein the device comprises means for performing measurements on a plurality of calibration whole blood samples, wherein the measurements include, for each of the plurality of calibration whole blood samples:

measuring an haematocrit level in the calibration whole blood sample;

measuring a total analyte amount in the calibration whole blood sample; an measuring an analyte amount in a plasma sample obtained from the calibration whole blood sample; and means for calculating polynomial coefficients of a calibrated relation:

$$D_P=P_a(D_{ST},D_H)$$

from values of haematocrit level and analyte amount measured in the plurality of calibration whole blood samples, and values of analyte amount measured in the plasma samples from the plurality of calibration whole blood samples, where $D_p$ is the measured analyte amount in plasma, $D_{ST}$ is the measured analyte amount in whole blood, $D_H$ is the measured haematocrit level, and $P_a$ is a non-constant polynomial of a degree greater than or equal to 1 having as indeterminate values the measured analyte amount, $D_{ST}$, and the measured haematocrit level, $D_H$, the polynomial coefficients depending on the analyte, wherein, after calibration, the device, upon receiving a measurement of a total analyte amount in a whole blood sample, calculates a corrected analyte amount according to the calibrated relation $D_P=P_a(D_{ST}, D_H)$, where $D_p$ is the corrected analyte amount in plasma, $D_{ST}$ is the measured analyte amount, and $D_H$ is the measured haematocrit level.

8. A device for measuring the plasmatic analyte concentration in a whole blood sample, wherein the device comprises means for performing measurements on a plurality of calibration whole blood samples, wherein the measurements include, for each of the plurality of calibration whole blood samples:

measuring an haematocrit level in the calibration whole blood sample;

measuring an analyte amount in the calibration whole blood sample, and obtaining a total analyte concentration obtained from the total analyte amount measured in the calibration whole blood sample; and measuring an analyte amount in a plasma sample obtained from the calibration whole blood sample, and obtaining an analyte concentration from the analyte amount measured in the plasma sample; and means for calculating polynomial coefficients of a calibrated relation:

$$C_P=P_a(C_{ST},D_H)$$

from values of haematocrit level and analyte concentration measured in the plurality of calibration whole blood samples, and values of analyte concentration measured in the plasma samples from the plurality of calibration whole blood samples, where $C_p$ is the analyte concentration calculated from the measured analyte amount in plasma, $C_{ST}$ is the analyte concentration calculated from the measured analyte amount in whole blood, $D_H$ is the measured haematocrit level, and $P_a$ is a non-constant polynomial of a degree greater than or equal to 1 having as indeterminate values the measured analyte concentration, $C_{ST}$, and the measured haematocrit level, $D_H$, the polynomial coefficients depending on the analyte, wherein, after calibration, the device, upon receiving a measurement of a total analyte concentration in a whole blood sample, calculates a corrected analyte concentration according to the calibrated relation $C_P=P_a(C_{ST}, D_H)$, where $C_p$ is the corrected analyte concentration in plasma, $C_{ST}$ is the measured analyte concentration, and $D_H$ is the measured haematocrit level.

\* \* \* \* \*